US011547578B2

United States Patent
Malcolmson et al.

(10) Patent No.: US 11,547,578 B2
(45) Date of Patent: *Jan. 10, 2023

(54) IMPLANT INSERTION INSTRUMENT

(71) Applicant: Alphatec Spine, Inc., Carlsbad, CA (US)

(72) Inventors: George Malcolmson, Carlsbad, CA (US); Yang Cheng, Foothill Ranche, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 293 days.

This patent is subject to a terminal disclaimer.

(21) Appl. No.: 16/908,368

(22) Filed: Jun. 22, 2020

(65) Prior Publication Data
US 2020/0315815 A1    Oct. 8, 2020

Related U.S. Application Data

(63) Continuation of application No. 15/017,130, filed on Feb. 5, 2016, now Pat. No. 10,792,168.

(60) Provisional application No. 62/112,773, filed on Feb. 6, 2015.

(51) Int. Cl.
    *A61F 2/46*      (2006.01)
    *A61F 2/30*      (2006.01)

(52) U.S. Cl.
    CPC ..... *A61F 2/4611* (2013.01); *A61F 2002/3082* (2013.01); *A61F 2002/30507* (2013.01); *A61F 2002/30522* (2013.01); *A61F 2002/4627* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,716,415 | A * | 2/1998 | Steffee | A61F 2/4611 623/17.16 |
| 6,159,215 | A * | 12/2000 | Urbahns | A61F 2/4684 606/86 R |
| 6,174,311 | B1 | 1/2001 | Branch | |
| 6,319,257 | B1 | 10/2001 | Carignan | |
| 6,761,743 | B1 | 7/2004 | Johnson | |
| 7,905,886 | B1 | 3/2011 | Curran | |
| 9,351,845 | B1 | 5/2016 | Pimenta | |
| 10,729,560 | B2 * | 8/2020 | Baker | A61F 2/4657 |
| 10,888,433 | B2 * | 1/2021 | Frasier | A61F 2/447 |

(Continued)

*Primary Examiner* — Matthew J Lawson
(74) *Attorney, Agent, or Firm* — Robert Winn (57) ABSTRACT

An implant insertion instrument, and an implant are provided. The instrument includes a handle, a sleeve mounted to a distal end of the handle, and an implant rod disposed within the sleeve. The implant rod includes a gripper disposed on a distal end of the implant rod. The gripper has a first prong spaced apart from a second prong, the second prong being longer than the first prong. The implant includes an implant body, the implant body having a convex surface opposite a concave surface wherein an outer surface of the implant is continuous so as to prevent bone growth within the implant. Accordingly, the instrument facilitates the engagement of the implant by a simple push of the sleeve. Further, the implant has a continuous surface so as to inhibit bone growth and facilitate removal of the implant from the surgical site.

18 Claims, 12 Drawing Sheets

(56) References Cited

U.S. PATENT DOCUMENTS

| | | |
|---|---|---|
| 2006/0235426 A1 | 10/2006 | Lim |
| 2007/0162128 A1 | 7/2007 | DeRidder |
| 2010/0249797 A1 | 9/2010 | Trudeau |
| 2010/0286784 A1 | 11/2010 | Curran |
| 2011/0106259 A1 | 5/2011 | Lindenmann |
| 2011/0112587 A1 | 5/2011 | Patel |
| 2011/0264152 A1 | 10/2011 | Weiman |
| 2012/0078371 A1 | 3/2012 | Gamache |
| 2012/0083884 A1 | 4/2012 | Miltz |
| 2012/0083885 A1 | 4/2012 | Thibodeau |
| 2012/0185045 A1 | 7/2012 | Morris |
| 2012/0197317 A1 | 8/2012 | Lezama |
| 2012/0277810 A1 | 11/2012 | Siccardi |
| 2013/0204370 A1 | 8/2013 | Danacioglu |
| 2015/0173808 A1 | 6/2015 | Sack |
| 2016/0030195 A1 | 2/2016 | Prevost |

\* cited by examiner

IMPLANT INSERTION INSTRUMENT

CROSS-REFERENCE TO RELATED APPLICATIONS

This application is a continuation application of U.S. application Ser. No. 15/017,130, filed Feb. 5, 2016, which claims priority to U.S. Provisional Application No. 62/112,773, filed Feb. 6, 2016, the contents of both of which are incorporated herein by reference.

TECHNICAL FIELD

An implant insertion instrument having an implant rod with a gripper configured to engage an implant and a mechanism for tightening the grip of the gripper on the implant is provided.

BACKGROUND

Implant insertion instruments for gripping an implant and inserting the implant to perform a surgical procedure are known. Currently such implant instruments include a gripping mechanism configured to tighten the instrument's hold on the implant. Current gripping mechanisms are actuated by the user engaging the instrument with a pair of his/her fingers. Further, current implant instruments secure the implant by pinching the distal edges of the implant and threadingly engaging the implant.

Current grippers include a stub threadably engaged to an opening of the implant and a pair of grippers having a notched edge engaged to a notch adjacent the opening configured. The notched adjacent the opening is configured to receive the notched edge of the gripper. However, such openings in the implant may provide an opportunity for bone growth wherein extraction of the implant may be made difficult by the interwoven bone growth. Accordingly, it remains desirable to have an implant and an implant inserting instrument configured to grip the implant without the use of an opening for providing a snap fit engagement and accommodating a threaded stud.

SUMMARY

An implant insertion instrument configured to be operated by a single user is provided. The instrument includes a handle configured to both tighten the grip on the implant and fix the gripping force applied to the implant by simple rotation of the handle. The handle is configured to be gripped by the entire hand of the user so as to reduce the force required to tighten the grip on the implant relative to the use of individual fingers. Further, the instrument is configured to exert a tightening force on the implant with relatively less rotation than the implant instruments currently known and used in the art.

The instrument includes an implant rod. The implant may have a double threaded end opposite a gripper. The implant rod is disposed within a sleeve. The sleeve is a generally cylindrical member having a guide housing disposed on a distal end and a first housing. The first housing is disposed on the proximal end of the sleeve.

The gripper is configured to engage and retain an implant. As shown, the implant is a generally kidney-shaped body having a convex surface opposite a concave surface. The gripper is configured to engage opposing sides of the implant.

The gripper includes a first prong spaced apart from a second prong. A slit defines the first prong from the second prong. The inner surface of the first prong may include a gripping feature such as a plurality of ribs. The second prong is configured to engage the concave surface and has a length generally the same length as the concave surface of the implant. The first prong has a length which is shorter than the second prong and is configured to engage the apex of the convex surface of the implant.

The instrument includes a drive mechanism and a locking mechanism. The drive mechanism is configured to axially move the implant rod within a sleeve. The drive mechanism may include a carrier. The carrier includes a threaded bore configured to engage the double lead threads of the implant rod. The carrier includes a stem configured to be fixedly seated within an opening of a handle.

The locking mechanism is configured to automatically fix a gripping tension the gripper exerts on the implant. For use herein the term "gripping tension" refers to the pinching force the first prong and the second prong exert on the sides of the implant. The locking mechanism may do so by fixing the axial position of the implant rod with respect to the bore of the sleeve. The locking mechanism may include a button working in concert with a locking ring. The button and the locking ring each have a plurality of teeth have a front face and a complimentary ramped shaped back wall so as to allow the button to freely traverse the locking ring in one direction and prevent the button from traversing the locking ring in the other direction.

The instrument may further include a hammer support insert. The hammer support insert is mounted to the proximal end of the handle. The hammer support insert includes a neck configured to support a hammer. The hammer may be configured to apply a downward force to help drive the implant into the surgical site, and also an outward force so as to help remove the implant from the body.

In operation, the drive mechanism is actuated by rotation of the handle, wherein the threaded end of the implant rod engages the threaded bore of the carrier. The axial displacement of the implant rod draws the gripper into the guide housing of the sleeve thus pinching the first prong against the second prong so as to grip the implant therebetween. As the handle is turned the teeth of the button traverse the teeth of the locking ring, wherein the axial displacement of the implant rod is fixed when the user stops rotating the handle. Accordingly, it should be further appreciated that depression of the button spaces the teeth of the button apart from the teeth of the locking mechanism so as to allow the handle to be rotated either clockwise or counterclockwise so as to tune the tension with respect to the gripper and the implant.

BRIEF DESCRIPTION OF THE DRAWINGS

The embodiments set forth in the drawings are illustrative and exemplary in nature and not intended to limit the subject matter defined by the claims. The detailed description of the illustrative embodiments can be better understood when read in conjunction with the following drawings where like structures are indicated with like reference numerals and in which:

DETAILED DESCRIPTION

The embodiments described herein generally relate to an implant insertion instrument configured to grip the outer edges of an implant and to facilitate the surgical procedures by reducing the time to securely engage the implant to the implant instrument.

The instrument includes a handle configured to be gripped by the user. The instrument further includes an implant rod having a gripper configured to hold an implant. A proximal end of the implant rod is threaded. The implant rod may be disposed within a sleeve. The gripper includes a first prong and a second prong separated by a slit extending along the axis of the implant rod. The second prong is longer than the first prong. The proximal end of the implant rod may be double threaded.

The handle is configured to actuate both a locking mechanism and a drive mechanism. The drive mechanism is configured to axially displace an implant rod within the sleeve. The locking mechanism is configured to automatically lock the implant rod along a predetermined position so as to exert a desired pressure between the gripper and the implant.

The distal end of the sleeve includes a guide housing. The guide housing is dimensioned so as to close the first prong towards the second prong when the implant rod travels towards the handle. The proximal end of the sleeve includes a first housing. A locking ring is disposed on an outer surface of the first housing and includes a plurality of teeth.

The locking mechanism may include a button configured to engage the teeth of the locking ring. The button is sandwiched between the teeth and a carrier. The carrier is fixedly mounted to a handle and is dimensioned so as to seatingly engage the button. The carrier may include a threaded bore configured to threadingly engage the threaded end of the implant rod.

A biasing member is disposed between the carrier and the button. The biasing member continuously urges the button into engagement with the locking ring. Rotation of the handle engages the threaded end of the implant rod, drawing the implant rod into a threaded bore of the carrier. As the gripper is advanced inwardly into the guide housing, the shoulders of the guide housing compress the first and second prongs together so as to pinch the implant therebetween.

In operation the user may grasp the handle with one hand and hold the gripper with the other. The implant may be seated between the first and second prongs of the gripper. The user simply rotates the handle thereby fixing the double threaded end of the implant rod so as to allow the double threaded end of the implant rod to engage with the threaded bore of the carrier. The rotation of the handle therein draws the implant rod inwardly wherein the shoulders of the guide housing close the first and second prongs towards each other pinching opposing outer surfaces of the implant therebetween. Upon achieving a desired gripping tension, the user simply stops rotating the handle. The biasing member is free to urge the button towards the locking ring, wherein the teeth of the button are engaged with the teeth of the locking ring, fixing the axial position of the implant rod with respect to the sleeve. More specifically, fixing the neck of the gripper within the guide housing of the sleeve.

Figure 1:
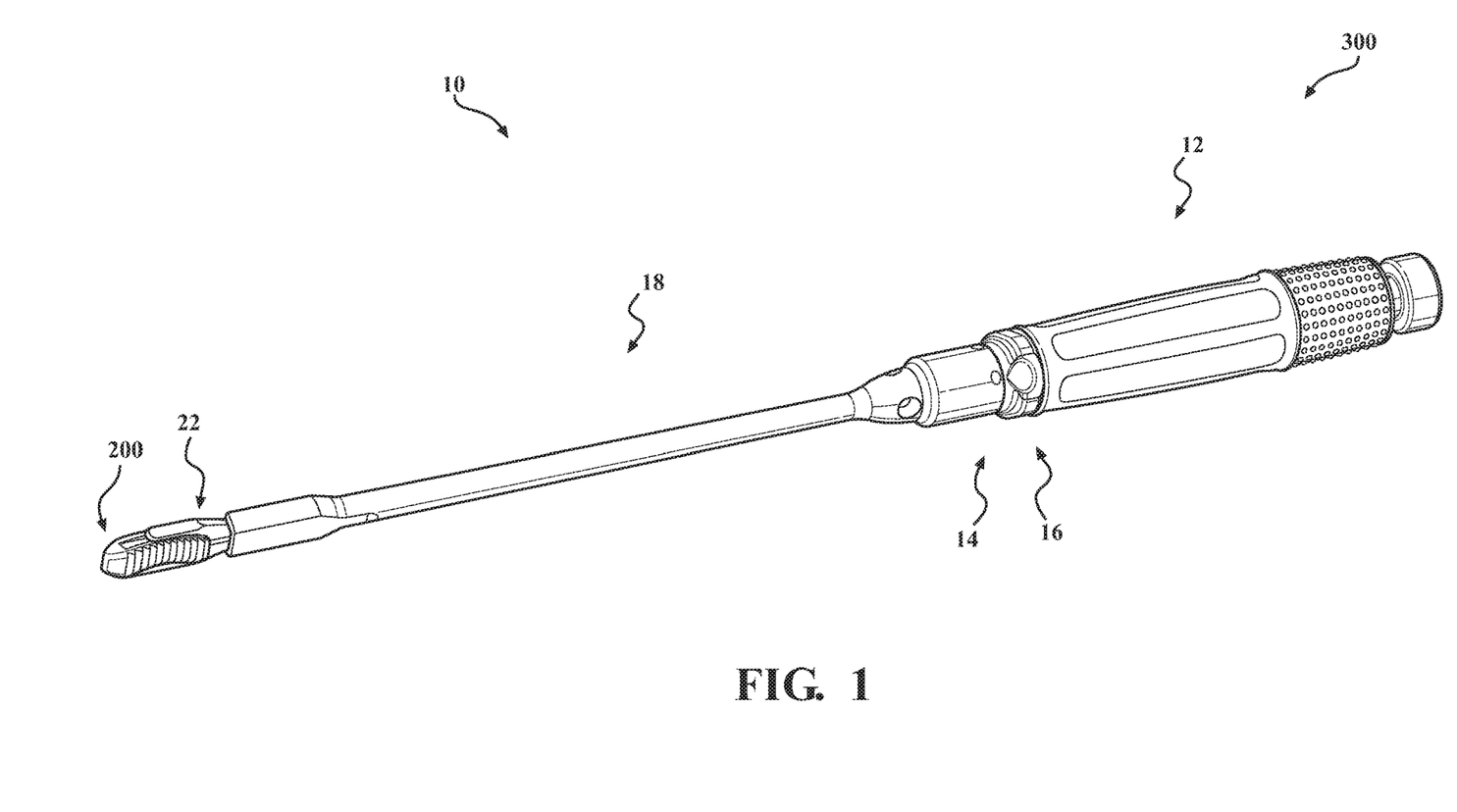
FIG. 1 is a perspective view of the implant insertion instrument.
Figure 2:
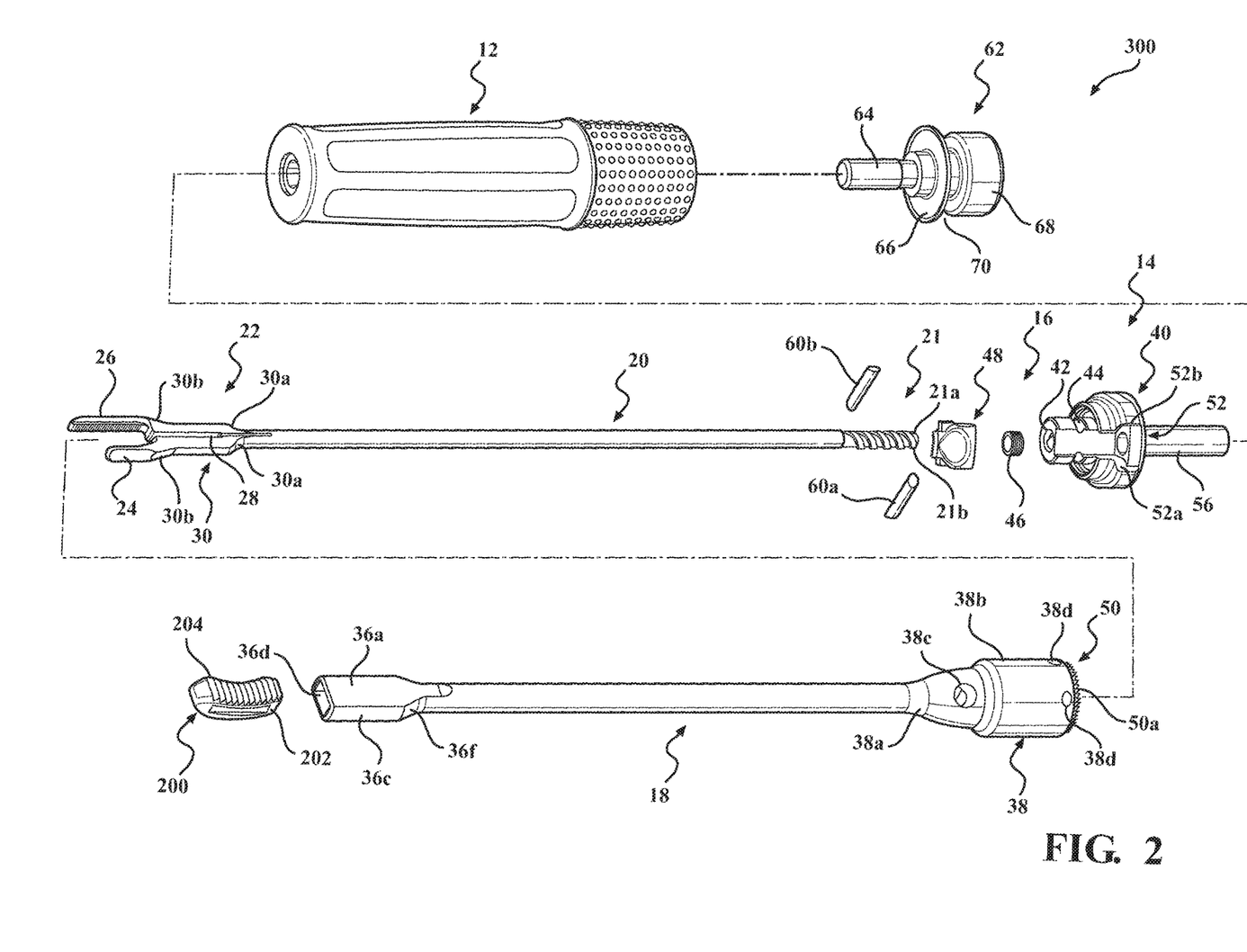
FIG. 2 is an exploded view of the instrument shown in FIG. 1.

With reference now to FIGS. 1 and 2, a perspective view and exploded view of an illustrative embodiment of the instrument 10 are provided. The instrument 10 may be formed of a polyether ketone, titanium, or any other material having sufficient structural rigidity to support implantation of the implant 200 and which is also approved for medical use. The instrument 10 includes a handle 12, a drive mechanism 14, a locking mechanism 16, a sleeve 18, and an implant rod 20.

The implant rod 20 includes a gripper 22 configured to engage the outer surfaces of the implant 200. The gripper 22 is disposed on a distal end of the implant rod 20. The implant rod 20 includes a proximal end 21 opposite the gripper 22. The proximal end 21 is threaded. Preferably, the end portion 21 is double threaded.

The gripper 22 includes a first prong 24 and a second prong 26. A slit 28 divides the first prong 24 from the second prong 26. A neck portion 30 is formed having angled surfaces opposite the first and second prongs 24, 26. The first prong 24 is configured to engage a convex surface 202 of the implant 200 and the second prong 26 is configured to engage the concave surface 204 of the implant 200. The second prong 26 is longer in length than the first prong 24.

With reference again to FIG. 2 and now to FIGS. 3, 4, 5, and 6, a description of the implant rod 20 is provided. The implant rod 20 is a generally cylindrical member having a solid body. The proximal end 21 of the implant rod 20 may be double threaded, meaning there are two threads 21a, 21b disposed on the outer surface of the implant rod 20, so as to form what is commonly referenced in the art as a double lead. The distal end of the implant rod 20 includes a gripper 22.

The slit 28 extends along the distal end of the implant rod 20 bisecting the gripper 22 along its axial length so as to define the first prong 24 and the second prong 26. The neck portion 30 includes a pair of first shoulders 30a disposed on opposing sides of the gripper 22. Each first shoulder 30a forms a ramp-shaped surface contiguous with the implant rod 20. A pair of second shoulders 30b is formed on opposing sides of the gripper 22. The second shoulders 30b extends outwardly and is contiguous with a respective one of the first and second prongs 24, 26.

The inner surfaces of the first and second prongs 24, 26 include a gripping feature 24a, 26a respectively. The gripping feature 24a, 26a may be a plurality of ridges configured to facilitate a friction engagement between the first and second prongs 24, 26 and respective convex and concave surfaces 202, 204 of the implant 200. The outer surface of the distal ends of the first and second prongs 24, 26 may be slanted so as to facilitate the insertion of the implant 200 into body tissue.

Figures 3, 4:
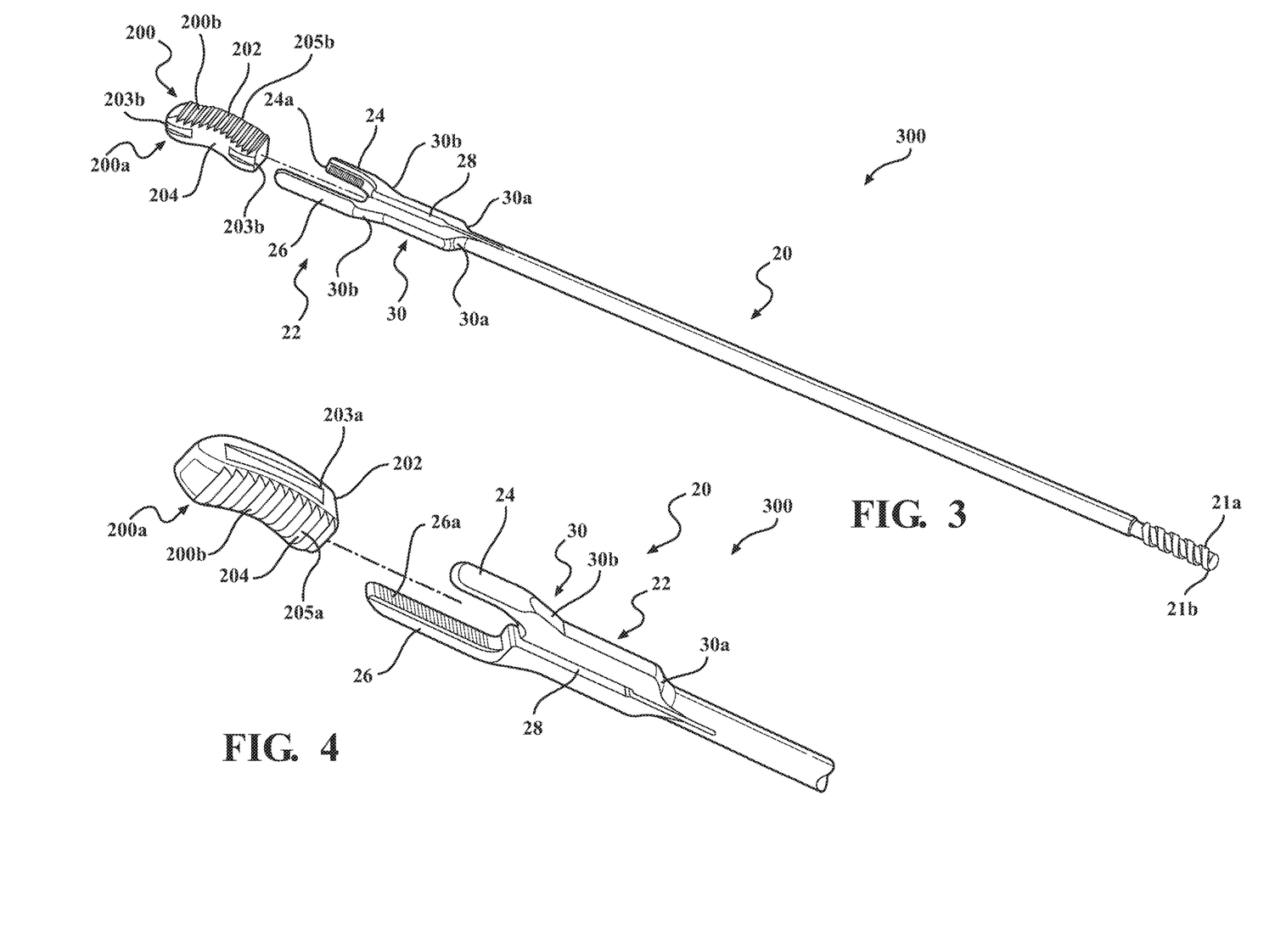
FIG. 3 is an isolated view of the implant rod and the implant.
FIG. 4 is an isolated view of the gripper.

With reference now to FIGS. 3 and 4, an illustrative perspective of an implant 200 is provided. The implant 200 has a generally kidney bean shaped body 200a. The body 200a has a convex surface 202 opposite a concave surface 204. Each of the convex and concave surfaces 202, 204 forming the sides of the implant 200. The implant 200 having a top surface 205a opposite a bottom surface 205b. The top surface 205a and the bottom surface 205b have a plurality of teeth 200b configured to help retain the implant 200 between adjacent vertebrae. The convex surface 202 and the concave surface 204 include respective first slot 203a and a second slot 203b configured to receive the gripper 22. The first slot 203a is continuous so as to engage a continuous surface of the first prong 24. Second slot 203b is formed of a first slot portion 203b-1 and a second slot portion 203b-2 disposed on a common plane. The outer surface of the implant 200 is continuous so as to prevent bone growth within the implant. The distal end 200c of the implant 200 is tapered so as to assist with implantation of the implant 200 into the vertebrae.

Figures 5, 6:
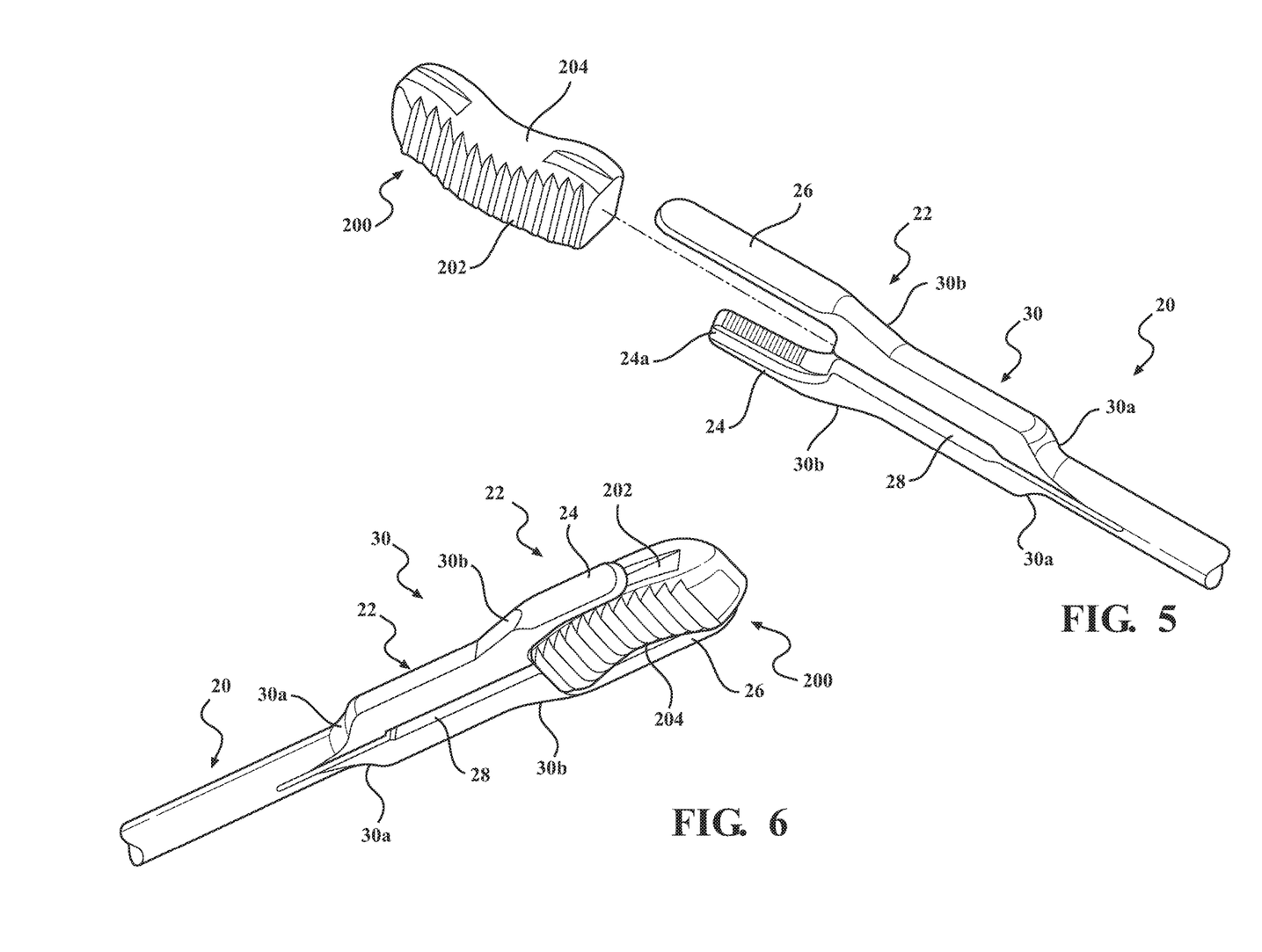
FIG. 5 is a view of FIG. 4 taken from an opposite perspective.
FIG. 6 is a view showing the gripper engaged with the implant.

With reference now to FIG. 6, the gripper 22 is shown engaged with the implant 200. As is shown, the first prong 24 is dimensioned in length so as to have the distal end of the first prong 24 engage the apex of convex surface 202 the implant 200. The second prong 26 is dimensioned in length so as to cover generally the entire length of the concave surface 204 of the implant 200. The second prong 26 and the first prong 24 are generally planar members.

As is shown in FIG. 6, space is formed between a mid-portion of the second prong 26 and the mid portion of the concave surface 204 of the implant 200. The first prong 24 is configured to generally engage the apex of the convex surface 202. Preferably, the first prong 24 does not advance past the apex so as to form a catch which may tear soft tissue as the instrument 10 is being inserted into the body. FIG. 6 also shows the slit 28. The slit 28 may be compressed, closing the first and second prongs 24, 26 together with varying force so as to vary the gripping tension exerted by respective first and second prongs 24, 26 on the implant 200.

Figure 7:
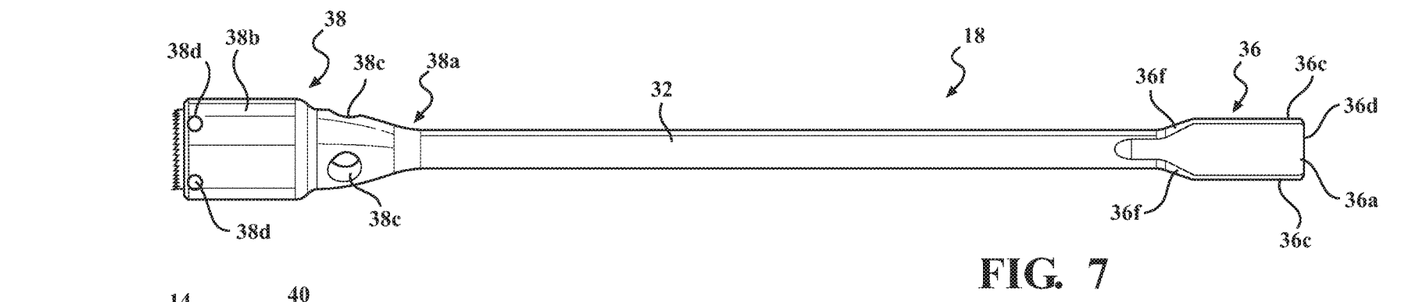
FIG. 7 is an isolated view of the sleeve.
Figure 15:
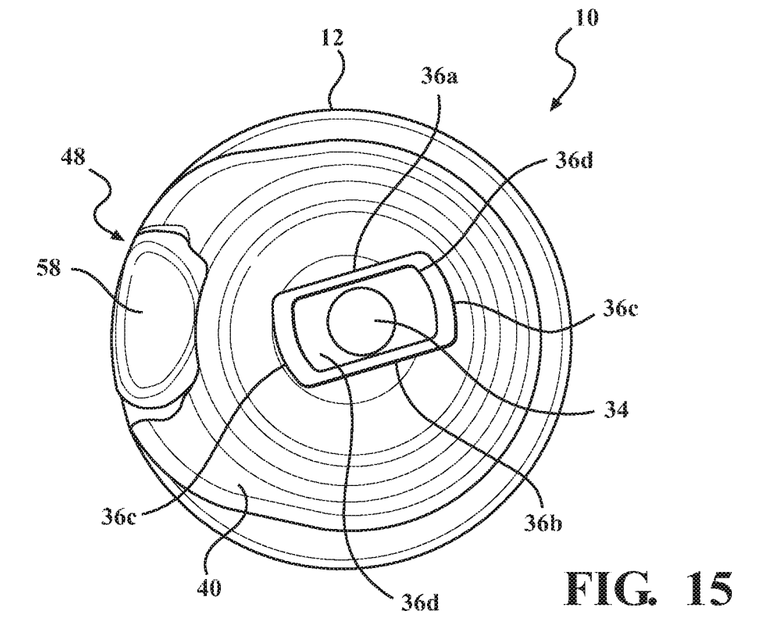
FIG. 15 is an end view of the instrument showing the bore of the sleeve.
Figure 16:
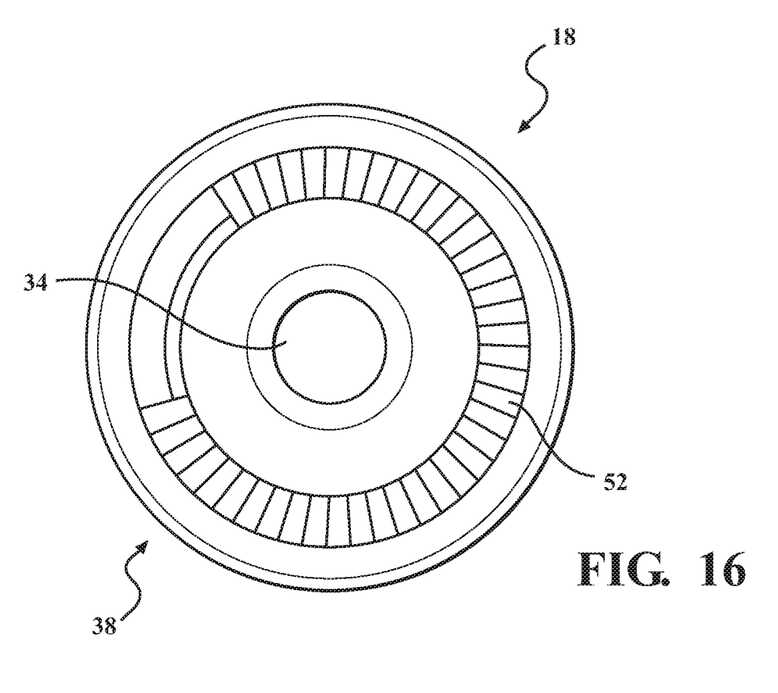
FIG. 16 is an end view of the sleeve showing the locking ring.

With reference again to FIG. 1, and now to FIGS. 7, 15 and 16, an illustrative view of the sleeve 18 is provided. The sleeve 18 includes a shaft 32 having a bore 34 (shown in FIG. 16) extending along the axis of the shaft 32. A guide housing 36 is disposed on the distal end of the shaft 32 and a first housing 38 is disposed on a proximal end of the shaft 32. The guide housing 36 and the first housing 38 may be integrally formed to the shaft 32.

The guide housing 36 is configured to receive the gripper 22. The guide housing 36 includes a top wall 36a, a bottom wall 36b, and a side wall 36c so as to define an opening 36d for receiving the gripper 22. The opening 36d is contiguous with the bore 34 of the sleeve 18. The top and bottom walls 36a, 36b are generally planar. A portion of the side wall includes a pair of ramp-shaped walls 36f angled obtusely with respect to the outer surface of the shaft 32. The ramp-shaped walls 36f are configured to channel the first and second prongs 24, 26. It should be appreciated that the first and second prongs 24, 26 are pressed together when the implant rod 20 travels towards the proximal end of the handle 12.

The first housing 38 includes a cone-shaped portion 38a and a cylindrical portion 38b. The cone-shaped portion 38a includes a plurality of holes 38c. The holes 38c are configured to facilitate cleaning of the sleeve 18. The cylindrical portion 38b of the first housing 38 is further dimensioned so as to fit the locking mechanism 16 and the drive mechanism 14. The cylindrical portion 38b includes a pair of through-holes 38d.

With reference now to FIGS. 8-14, an illustrative view of the drive mechanism 14 and locking mechanism 16 are provided. The locking mechanism 16 is configured to automatically lock the implant rod 20 with respect to the sleeve 18. The drive mechanism 14 is configured to move the implant rod 20 axially with respect to the sleeve 18. More specifically, the drive mechanism 14 is configured to translate a rotary motion of the handle 12 into the axial displacement of the implant rod 20. The drive mechanism 14 works in cooperation with the locking mechanism 16 wherein a rotation of the handle 12, displaces the implant rod 20 axially and automatically locks the implant rod 20 in place.

Figure 11:
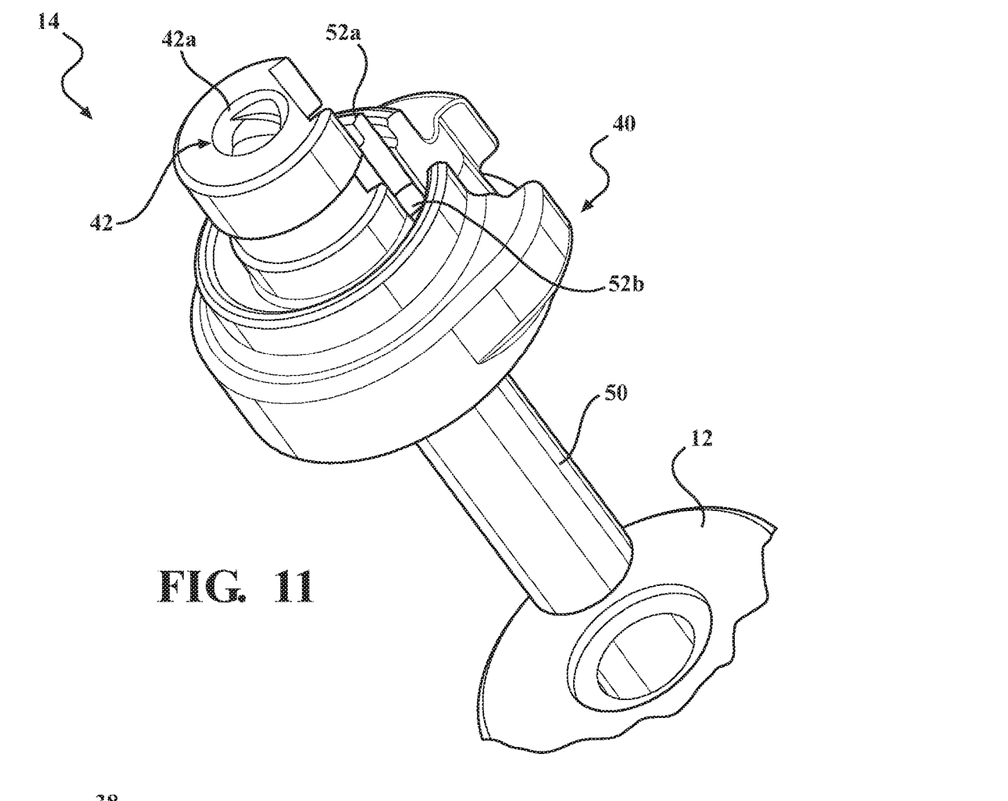
FIG. 11 is an isolated view of the carrier.

With reference now to FIGS. 11-4, an illustrative embodiment of the drive mechanism 14 is provided. The drive mechanism 14 is shown as a carrier 40. The carrier 40 includes a threaded bore 42 and a neck 44. The threaded bore 42 is configured to receive the threaded end 21 of the implant rod 20. For illustrative purposes, the threaded bore 42 of the carrier 40 has two leads (shown in FIG. 13) so as to receive both threads 21a, 21b of the implant rod 20. However, it should be appreciated that the implant rod 20 may have a single threaded end and in such cases, the threaded bore 42 may only include one lead.

With reference again to FIGS. 8-10, 12, 13 and 16, an illustrative embodiment of the locking mechanism 16 is provided. The locking mechanism 16 includes a biasing member 46, a button 48 and a locking ring 50. The biasing member 46 is disposed between an inner surface of the button 48 and an outer surface of the carrier 40, the biasing member 46 continuously urges the button 48 towards the locking ring 50. The button 48 includes a plurality of teeth 48a. The teeth 48a are disposed along a radius. The radius is complementary to the radius of the locking ring 50.

Figure 12:
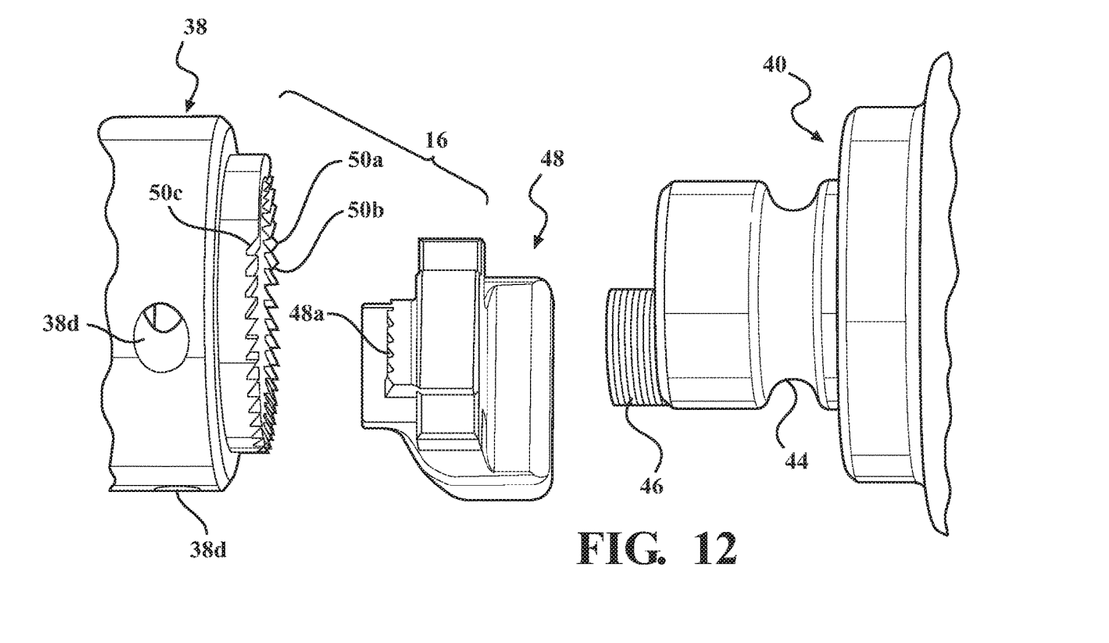
FIG. 12 is an exploded view showing the carrier, button, biasing member and locking ring.

An illustrative view of the locking ring 50 is provided in FIGS. 12 and 16. The locking ring 50 is formed on a peripheral edge of the first housing 38. The locking ring 50 includes a plurality of teeth 50a. The teeth 50a are ramp-shaped having a planar front face 50b and a slanted back wall 50c so as to allow the button 48 to traverse one way along the locking ring 50 wherein the front face 50b of the individual teeth 50a prevents the button 48 from being moved the opposite way. Thus it should be appreciated that rotation of the handle 12 along the ramp-shaped surfaces is permissible. However, rotation of the handle 12 against the front face of the locking ring 50 is prohibited by the engagement of the teeth of the button 48.

Figure 13:
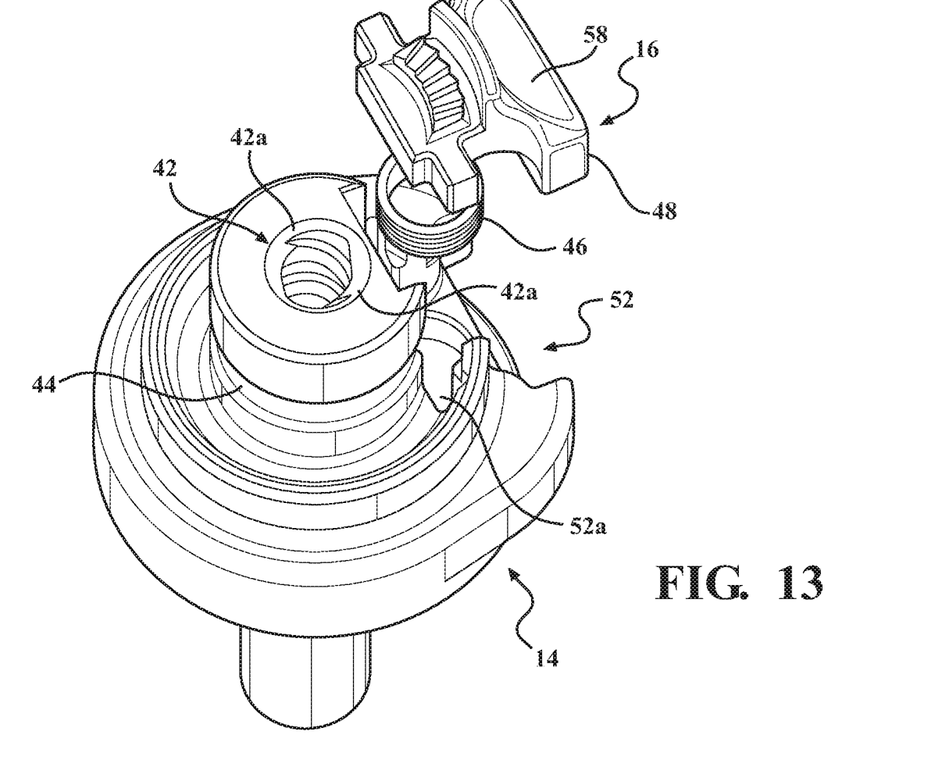
FIG. 13 is a different perspective view of FIG. 12.
Figure 14:
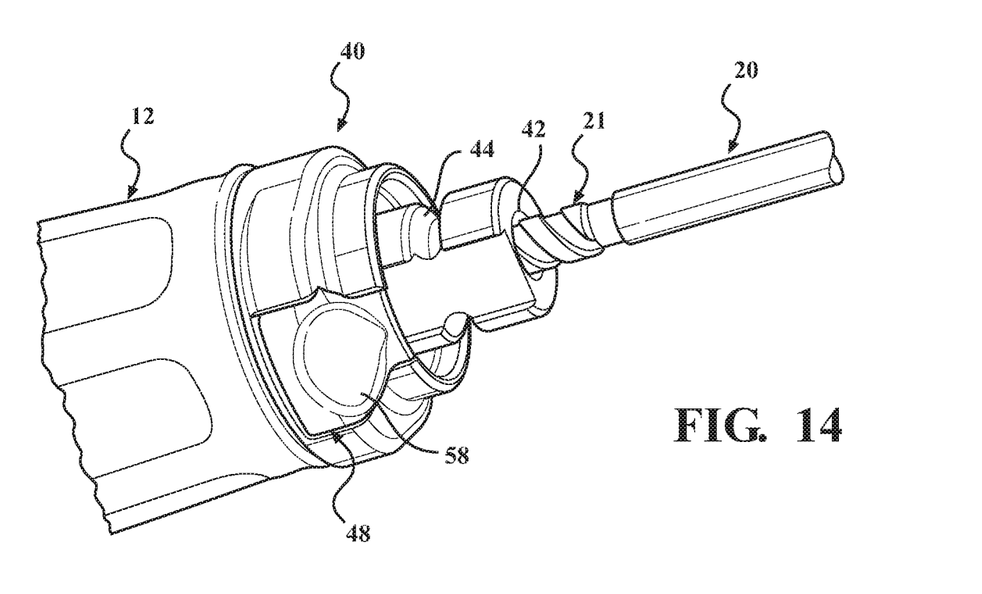
FIG. 14 is an isolated view showing the implant rod engaged with the carrier.

With reference now to FIGS. 11 and 13, an illustrative view of the carrier 40 is provided. The carrier 40 includes a seat portion 52 configured to hold a seating member 54 of the button 48. The seating member 54 of the button 48 may include a pair of extending members 54a, 54b configured to fittingly engage a pair of opposing slots 52a, 52b of the seat portion 52 of the carrier 40. Thus, the seat portion 52 prevents the button 48 from being rotated relative to the carrier 40.

Figure 8:
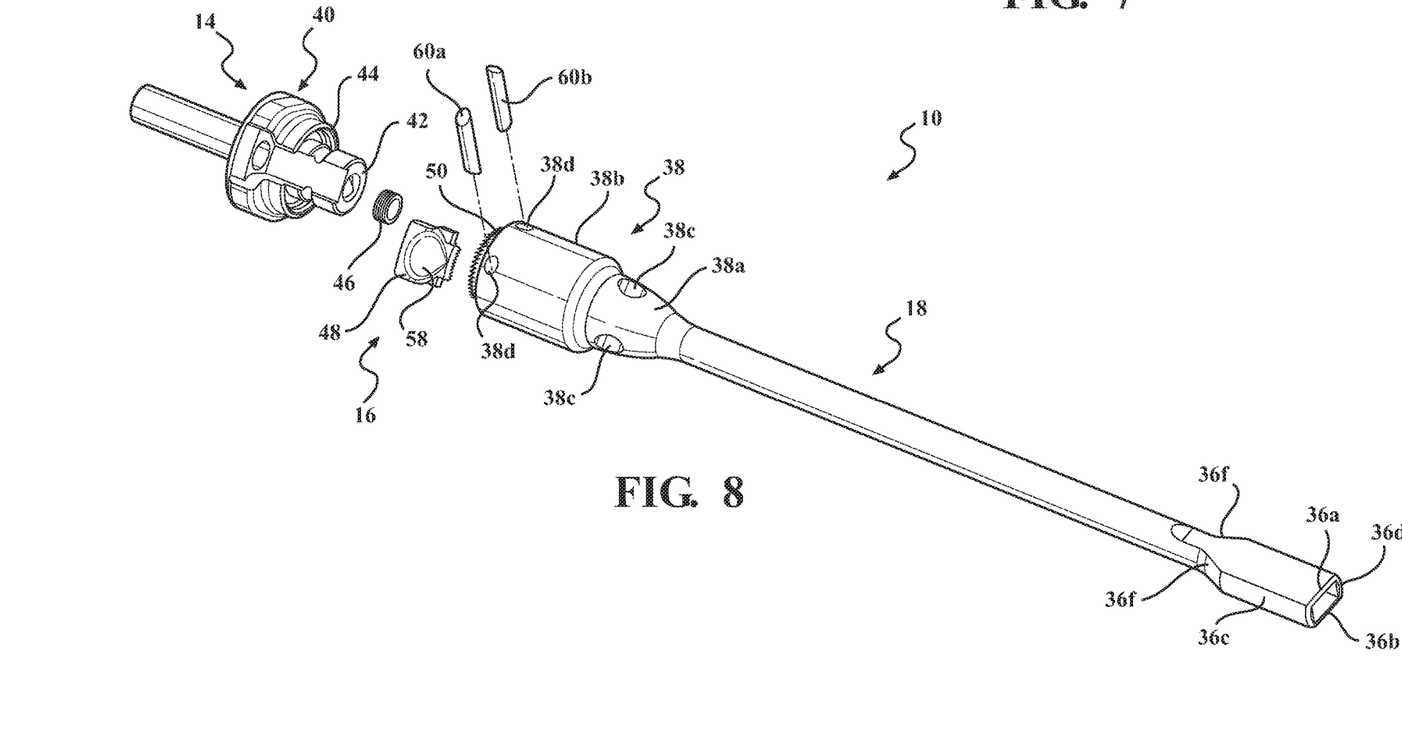
FIG. 8 is an exploded view of the drive mechanism and the locking mechanism.
Figure 9:
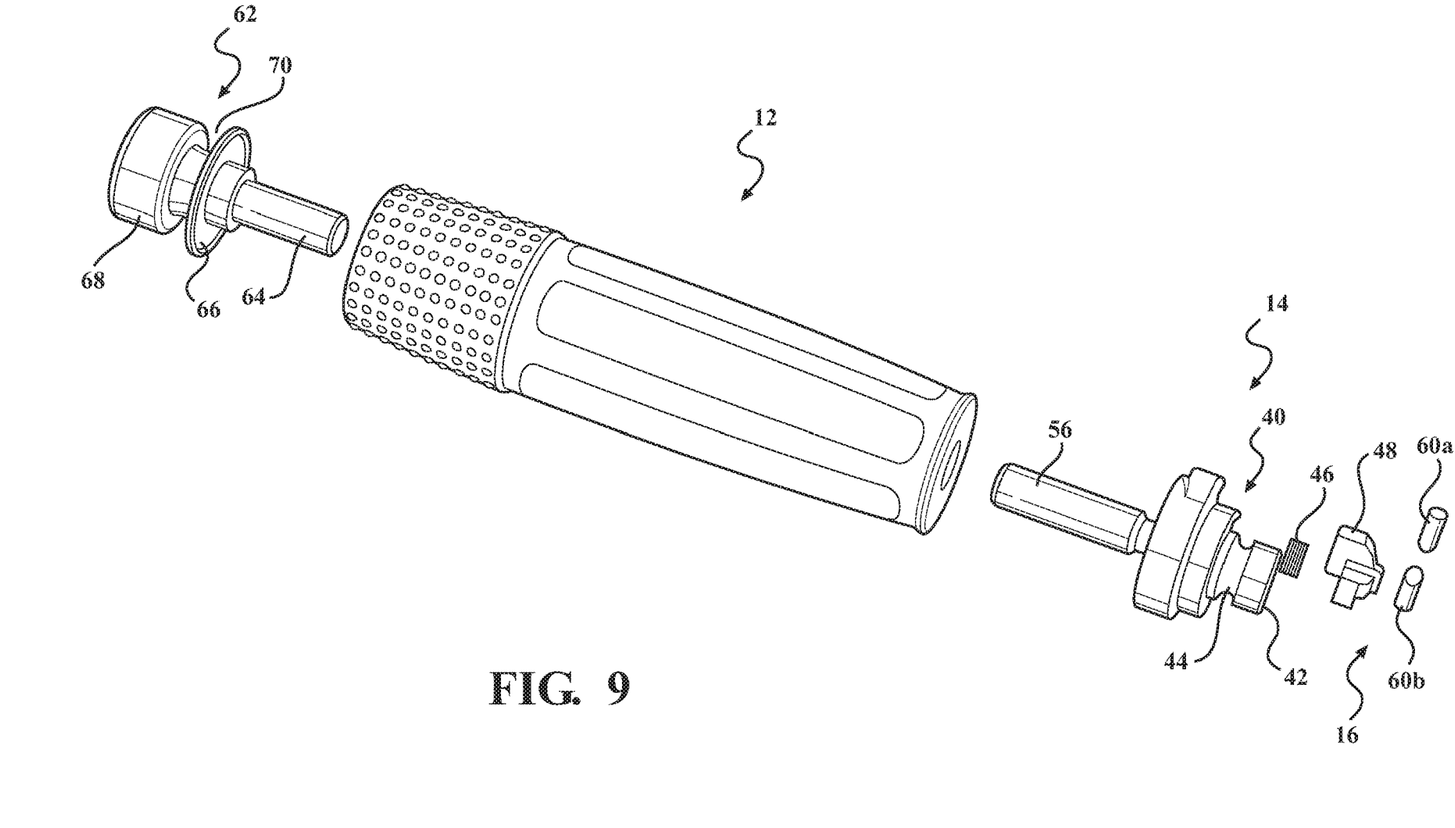
FIG. 9 is an exploded view of the hammer support insert, handle, carrier and button.
Figure 10:
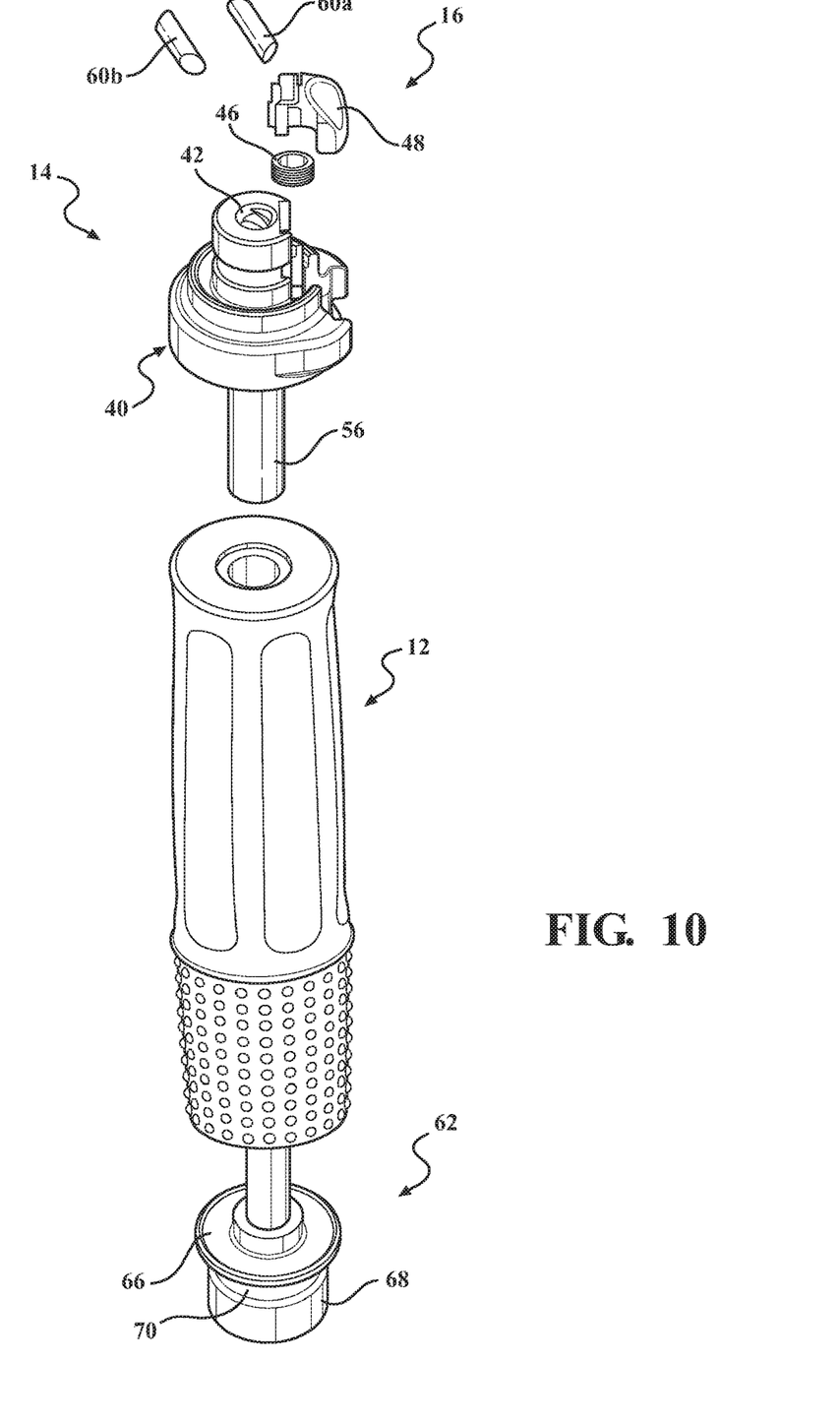
FIG. 10 is a view of FIG. 9 taken from a different angle.

The carrier 40 is held within the first housing 38, shown in FIG. 8. The first housing 38 includes a pair of through holes 38a, 38b configured to receive pins 60a, 60b. The pins 60a, 60b are configured to engage a neck 44 of the carrier 40 so as to retain the carrier 40 with respect to the first housing 38. The carrier 40 includes a stem 56 configured to be fixedly engage within an opening of the handle 12. Thus, the carrier 40 is rotatable with the handle 12 and axially fixed within the first housing 38 by the pins 60a, 60b.

With reference now to FIG. 14, the carrier 40 is shown mounted to the handle 12. The carrier 40 is fixed to the handle 12 and the button 48 is shown mounted within the seat portion 52 of the carrier 40. The biasing member 46 is hidden beneath the button 48. The button 48 includes a detent 58 formed on the outer surface of the button 48. The detent 58 may be dimensioned so as to fittingly receive a thumb. As shown, the carrier 40 includes a bore 42 having two thread receiving passages so as to receive the double threaded end of the implant rod 20. However, it should be appreciated that the bore 42 of the carrier 40 may only have a single thread in instances where the implant rod 20 has a single threaded end. FIG. 14 shows the implant rod 20 advanced within the threaded bore 42 of the carrier 40. Thus, it should be appreciated that when the implant rod 20 is held steady with one hand and the handle 12 is rotated with the other hand, the implant rod 20 may be advanced inwardly into the threaded bore 42 of the carrier 40.

With reference now to FIG. 15, a view of the distal end of the instrument 10 is shown wherein the guide housing 36 has a generally rectangular opening 36d and the bore 34 of the sleeve 18 is shown. The guide housing 36 is dimensioned so as to slidingly receive the neck portion 30 of the gripper 22.

Figure 19:
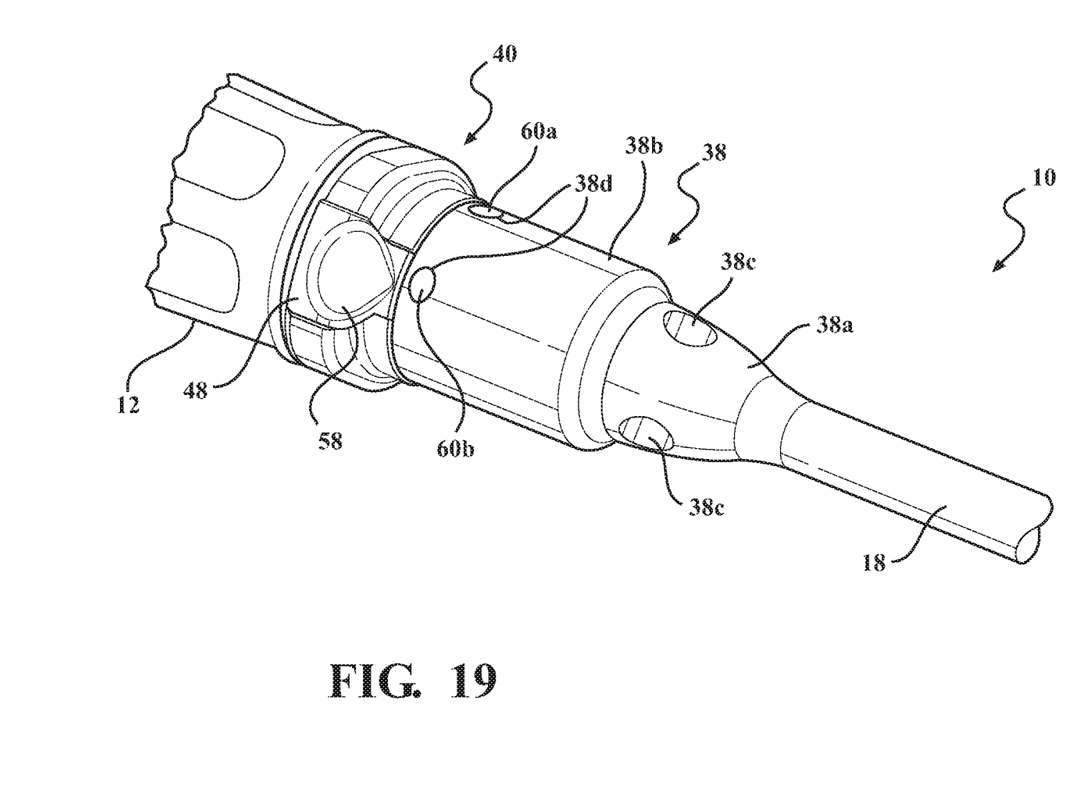
FIG. 19 is a view showing the handle, locking mechanism, and the sleeve mounted together.

With reference now to FIG. 19, the instrument 10 is shown with the sleeve 18 mounted to the carrier 40. FIG. 19 shows pins 60a, 60b mounted within the through holes 38a, 38b of the first housing 38. It should be appreciated that the pins 60a, 60b engage the neck 44 of the carrier 40 holding the carrier 40 axially fixed with respect to the first housing 38, but also allowing the carrier 40 to rotate within the first housing 38.

Figure 17:
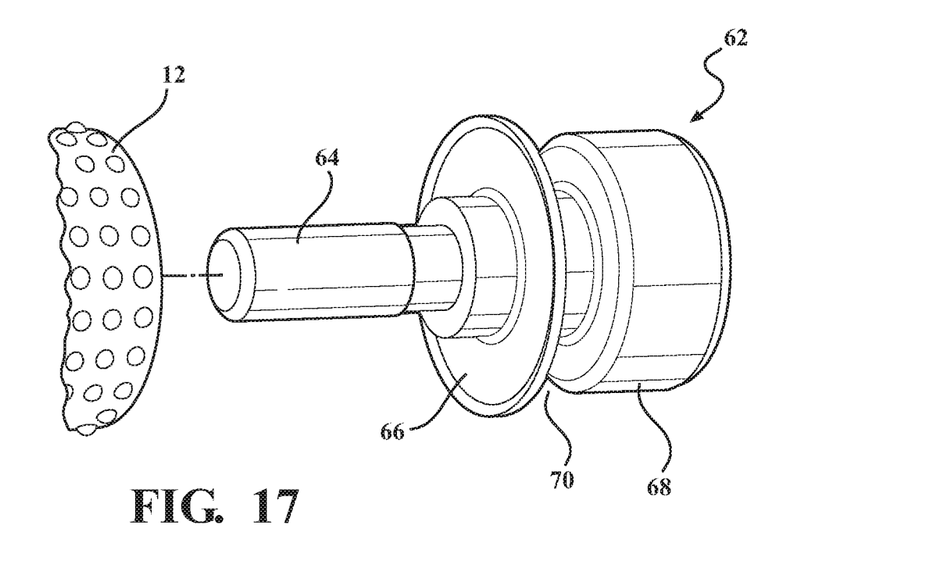
FIG. 17 is a perspective view showing the hammer support insert.
Figure 18:
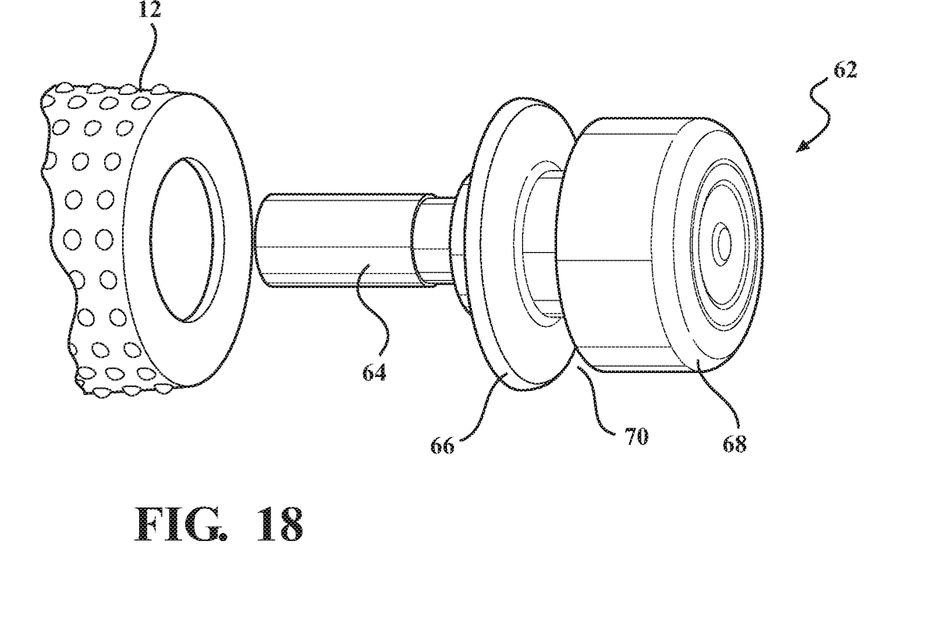
FIG. 18 is a view of FIG. 17 showing the neck of the hammer insert.

With reference now to FIGS. 17 and 18, a hammer support insert 62 is provided. The hammer support insert 62 includes a stem 64 configured to be fixedly mounted within an opening of the distal end of the handle 12. The hammer support insert includes a plate 66 spaced apart from a head 68 so as to define a neck portion 70. The neck portion 70 is configured to support a hammer (not shown) configured to drive the instrument 10 into or away from a body. Any hammer currently known and used may be adapted for use herein, illustratively including a hammer commonly referenced as a slap hammer. The neck portion 70 allows the user to attach the hammer to the instrument 10 regardless of the orientation of the instrument 10.

In operation, the user inserts the implant 200 into the gripper 22 of the implant rod 20 wherein the first and second prongs 24, 26 are engaged to a respective convex and concave surfaces 202, 204 of the implant 200. The user simply holds the implant rod 20 by the gripper 22 and slides the implant rod 20 into the bore 34 of the sleeve 18 wherein the neck portion 30 of the gripper 22 is fitted within the guide housing 36.

With the other hand the user simply turns the handle 12 thereby engaging the threaded end 21 of the insert implant rod 20 with the threaded bore 42 of the carrier 40. With each rotation the teeth 48a of the button 48 advance along the teeth 50a of the locking ring 50. Simultaneously, the implant rod 20 is advanced towards the proximal end of the handle 12 with respect to the threaded bore 42 of the carrier 40.

It should be appreciated that as the handle 12 is rotated the teeth 48a of the button 48 are slid over a respective backwall 50c of the teeth 50a of the locking ring 50. The biasing member 46 urges the button 48 towards the locking ring 50 placing the front face of the locking ring 50 in contact with a back surface of the tooth of the button 48. As the implant rod 20 travels towards the proximal end of the handle 12, the prongs are urged together by the ramp-shaped walls 36f of the guide housing 36 applying a tensioning force with respect to the first and second prongs 24, 26 on the implant 200. Upon generating a desired gripping force, the user may simply stop rotating the handle 12 wherein the locking mechanism 16 retains the gripping force by maintaining the axial position of the implant rod 20.

A system 300 for performing a medical procedure is also provided herein. The system 300 includes an instrument 10. The instrument 10 includes a handle 12, a drive mechanism 14, a locking mechanism 16, a sleeve 18, and an implant rod 20. An illustrative of the instrument 10 is shown in FIGS. 1-19.

The implant rod 20 includes a gripper 22 configured to engage the outer surfaces of the implant 200. The gripper 22 is disposed on a distal end of the implant rod 20. The implant rod 20 includes a proximal end 21 opposite the gripper 22. The proximal end 21 is threaded. Preferably, the end portion 21 is double threaded.

The gripper 22 includes a first prong 24 and a second prong 26. A slit 28 divides the first prong 24 from the second prong 26. A neck portion 30 is formed having angled surfaces opposite the first and second prongs 24, 26. The first prong 24 is configured to engage a convex surface 202 of the implant 200 and the second prong 26 is configured to engage the concave surface 204 of the implant 200. The second prong 26 is longer in length than the first prong 24.

With reference again to FIG. 2 and now to FIGS. 3, 4, 5, and 6, a description of the implant rod 20 is provided. The implant rod 20 is a generally cylindrical member having a solid body. The proximal end 21 of the implant rod 20 may be double threaded, meaning there are two threads 21a, 21b disposed on the outer surface of the implant rod 20, so as to form what is commonly referenced in the art as a double lead. The distal end of the implant rod 20 includes a gripper 22.

The slit 28 extends along the distal end of the implant rod 20 bisecting the gripper 22 along its axial length so as to define the first prong 24 and the second prong 26. The neck portion 30 includes a pair of first shoulders 30a disposed on opposing sides of the gripper 22. Each first shoulder 30a forms a ramp-shaped surface contiguous with the implant rod 20. A pair of second shoulders 30b is formed on opposing sides of the gripper 22. The second shoulders 30b extends outwardly and is contiguous with a respective one of the first and second prongs 24, 26.

The inner surfaces of the first and second prongs 24, 26 include a gripping feature 24a, 26a respectively. The gripping feature 24a, 26a may be a plurality of ridges configured to facilitate a friction engagement between the first and second prongs 24, 26 and respective convex and concave surfaces 202, 204 of the implant 200. The outer surface of the distal ends of the first and second prongs 24, 26 may be slanted so as to facilitate the insertion of the implant 200 into body tissue.

The system 300 further includes an implant. FIGS. 3 and 4, provides an illustrative perspective of an implant 200 for use in the system 300. The implant 200 has a generally kidney bean shaped body 200a. The body 200a has a convex surface 202 opposite a concave surface 204. Each of the convex and concave surfaces 202, 204 forming the sides of the implant 200. The implant 200 having a top surface 205a opposite a bottom surface 205b. The top surface 205a and the bottom surface 205b have a plurality of teeth 200b configured to help retain the implant 200 between adjacent vertebrae. The sides 201*a*, 201*b* includes a slot 203*a*, 203*b* configured to receive the gripper 22. The first slot 203*a* is continuous so as to engage a continuous surface of the first prong 24. Second slot 203*b* is formed of a first slot portion 203*b*-1 and a second slot portion 203*b*-2 disposed on a common plane. The outer surface of the implant 200 is continuous so as to prevent bone growth within the implant. The distal end 200*c* of the implant 200 is tapered so as to assist with implantation of the implant 200 into the vertebrae.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination.

The invention claimed is:

1. An implant insertion instrument configured to engage an implant during the performance of a surgical procedure, the implant insertion instrument comprising:
    a handle having a control portion;
    a sleeve fixedly mounted to a distal end of the handle;
    an implant rod disposed within the sleeve, the implant rod having a gripper disposed on a distal end of the implant rod, the gripper having a first prong spaced apart from a second prong;
    a drive mechanism configured to translate a rotation of the control portion in a first direction into an axial displacement of the implant rod within the sleeve, wherein when the implant rod travels towards the handle, the first prong closes against the second prong so as to secure the implant between the first and second prongs; and
    a locking mechanism configured to fix the implant rod with respect to the sleeve, the locking mechanism including a locking ring having a plurality of ramp-shaped teeth fixedly mounted to the implant rod and a button having a plurality of teeth, the button configured to lockingly engage the plurality of teeth of the locking ring so as to allow rotation of the control portion in the first direction while resisting rotation of the control portion in a direction opposite of the first direction and fix the implant rod with respect to the sleeve.

2. The implant insertion instrument as set forth in claim 1, wherein an inner surface of the first prong and the second prong includes a gripping feature.

3. The implant insertion instrument as set forth in claim 2, wherein the gripping feature is a plurality of ridges configured to facilitate a friction engagement between the first prong and the second prong and the implant.

4. The implant insertion instrument as set forth in claim 1, wherein the sleeve includes a guide housing disposed on the distal end of the sleeve, the guide housing having a ramp-shaped surface angled obtusely with respect to an outer surface of the sleeve, the ramp-shaped surface closing the first prong towards the second prong when the gripper is advanced into the guide housing.

5. The implant insertion instrument as set forth in claim 4, wherein the sleeve includes a shaft having a bore extending along the axis of the shaft.

6. The implant insertion instrument as set forth in claim 5, further including a guide housing disposed on the distal end of the shaft and a first housing is disposed on a proximal end of the shaft.

7. The implant insertion instrument as set forth in claim 6, wherein the drive mechanism is a carrier, the carrier has a threaded bore and a neck, the threaded bore is configured to receive a threaded end of the implant rod.

8. The implant insertion instrument set forth in claim 7, wherein the locking mechanism further includes a biasing member, the biasing member being disposed between an inner surface of the button and an outer surface of the carrier, the biasing member configured to continuously urge the button towards the locking ring.

9. The implant insertion instrument set forth in claim 8, wherein the threaded end of the implant rod is double threaded so as to have two lead threads, and wherein the threaded bore of the carrier is double threaded so as to receive a corresponding thread of the implant rod.

10. The implant insertion instrument as set forth in claim 1, wherein the sleeve includes a guide housing disposed on the distal end of the sleeve, wherein the first and second prongs each have a ramp-shaped surface configured to abut an internal surface of the guide housing such that when the implant rod travels towards the handle, the internal surface of the guide housing causes the first prong to close against the second prong.

11. A system for performing a medical procedure, the system comprising: the implant insertion instrument set forth in claim 1; and an implant.

12. The system of claim 11, wherein the implant has a convex surface opposite a concave surface.

13. The system of claim 11, wherein an outer surface of the implant is continuous so as to prevent bone growth within the implant.

14. The system as set forth in claim 11, wherein the implant includes a top surface opposite a bottom surface, the top surface and the bottom surface have a plurality of teeth configured to help retain the implant between adjacent vertebrae.

15. The system as set forth in claim 11, wherein concave surface includes a first slot and the convex surface includes a second slot, the first slot and the second slot are configured to receive the gripper.

16. The system as set forth in claim 15, wherein the first slot is continuous so as to engage a continuous surface of the first prong, and the second slot is formed of a first slot portion and a second slot portion, the first slot portion and the second slot portion are disposed on a common plane.

17. The system as set forth in claim 11, wherein a distal end of the implant is tapered.

18. An implant insertion instrument configured to engage an implant during the performance of a surgical procedure, the implant insertion instrument comprising:
    a handle having a control portion configured to rotate in a first direction;
    a sleeve fixedly mounted to a distal end of the handle;
    an implant rod disposed within the sleeve, the implant rod having a gripper disposed on a distal end of the implant rod, the gripper having a first prong spaced apart from a second prong;
    a drive mechanism configured to translate a rotation of the control portion in the first direction into an axial displacement of the implant rod so as to pull the first and second prongs within the sleeve towards the handle closing the first prong against the second prong so as to secure the implant between the first and second prongs; and
    a locking mechanism configured to allow rotation of the control portion in the first direction while resisting rotation of the control portion in a direction opposite the first direction so as to fix the implant rod relative to the sleeve.

* * * * *